(12) United States Patent
Stevens et al.

(10) Patent No.: US 10,709,407 B2
(45) Date of Patent: Jul. 14, 2020

(54) IMAGING PROTOCOL TRANSLATION

(71) Applicant: General Electric Company, Schenectady, NY (US)

(72) Inventors: Grant Morey Stevens, Waukesha, WI (US); Adam Budde, Waukesha, WI (US); Rinki Singh, Waukesha, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 815 days.

(21) Appl. No.: 14/458,572

(22) Filed: Aug. 13, 2014

(65) Prior Publication Data

US 2016/0045182 A1 Feb. 18, 2016

(51) Int. Cl.
*A61B 6/00* (2006.01)
*A61B 6/03* (2006.01)

(52) U.S. Cl.
CPC .............. *A61B 6/545* (2013.01); *A61B 6/032* (2013.01); *A61B 6/465* (2013.01); *A61B 6/5205* (2013.01); *A61B 6/566* (2013.01)

(58) Field of Classification Search
None
See application file for complete search history.

(56) References Cited

U.S. PATENT DOCUMENTS

| | | | |
|---|---|---|---|
| 5,671,070 A | 9/1997 | Przybylowicz et al. | |
| 7,376,183 B2 | 5/2008 | Weigand et al. | |
| 2005/0209888 A1* | 9/2005 | Oowaki | A61B 6/542 705/3 |
| 2008/0004904 A1 | 1/2008 | Tran | |
| 2008/0242968 A1* | 10/2008 | Claus | A61B 6/032 600/407 |
| 2009/0164474 A1 | 6/2009 | Noumeir | |
| 2009/0309874 A1* | 12/2009 | Salganicoff | G06T 19/00 345/419 |
| 2010/0286521 A1 | 11/2010 | Betts | |
| 2012/0213326 A1* | 8/2012 | Walker | A61B 6/032 378/4 |
| 2014/0072108 A1* | 3/2014 | Rohler | A61B 6/032 378/207 |

\* cited by examiner

*Primary Examiner* — Jeffrey G Hoekstra
*Assistant Examiner* — Jason M Ip
(74) *Attorney, Agent, or Firm* — Fletcher Yoder, P.C.

(57) ABSTRACT

Techniques for imaging protocol translation are described herein. The techniques may include data indicating a protocol for image capture of a first imaging device. The protocol includes parameters. The techniques may include translating the protocol of the first imaging device for use at a second imaging device by determining adjustments to be made to one or more of the parameters.

15 Claims, 8 Drawing Sheets

400

500

IMAGING PROTOCOL TRANSLATION

BACKGROUND OF THE INVENTION

The subject matter disclosed herein relates generally to techniques for diagnostic medical imaging, such as X-ray imaging, nuclear medicine imaging, and the like. In diagnostic medical imaging, systems may be configured with protocols. Each protocol may include multiple parameters for capturing an image using a diagnostic medical imaging system. Further, different vendors of diagnostic medical imaging systems, as well as different systems from a given vendor, may have features on their respective diagnostic medical imaging systems that impact image quality differently depending on a given imaging device model being used. When a given clinical environment, such as a hospital, switches, or incorporates, a new diagnostic medical imaging system, considerable time may be spent developing an understanding of the new diagnostic medical imaging system parameters.

BRIEF DESCRIPTION OF THE INVENTION

An embodiment relates to a method for imaging protocol translation. The method includes receiving data indicating a protocol for image capture of a first imaging device, wherein the protocol includes parameters. The method also includes translating the protocol of the first imaging device for use at a second imaging device by determining adjustments to be made to one or more of the parameters.

Another embodiment relates to a system for imaging protocol translation. The system includes a first imaging device, a second imaging device and a protocol translation module. The protocol translation module includes logic, at least partially including hardware logic, to receive data indicating a protocol for image capture of a first imaging device, wherein the protocol includes parameters. The logic is also configured to translate the protocol of the first imaging device for use at a second imaging device by determining adjustments to be made to one or more of the parameters.

Still another embodiment relates to a computer-readable medium for imaging protocol determination. The computer-readable medium includes processor-executable code to receive data indicating a protocol for image capture of a first imaging device, wherein the protocol includes parameters. The processor-executable code is also configured to translate the protocol of the first imaging device for use at a second imaging device by determining adjustments to be made to one or more of the parameters.

BRIEF DESCRIPTION OF THE DRAWINGS

The present techniques will become more fully understood from the following detailed description, taken in conjunction with the accompanying drawings, wherein like reference numerals refer to like parts, in which.

DETAILED DESCRIPTION OF THE INVENTION

In the following detailed description, reference is made to the accompanying drawings that form a part hereof, and in which is shown by way of illustration of specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the embodiments described herein.

As used herein, the terms "system," "unit," or "module" may include a hardware and/or software system that operates to perform one or more functions. For example, a module, unit, or system may include a computer processor, controller, or other logic-based device that performs operations based on instructions stored on a tangible and non-transitory computer readable storage medium, such as a computer memory. Alternatively, a module, unit, or system may include a hard-wired device that performs operations based on hard-wired logic of the device. Various modules or units shown in the attached figures may represent the hardware that operates based on software or hardwired instructions, the software that directs hardware to perform the operations, or a combination thereof.

Various embodiments provide techniques for translating imaging device protocols between imaging devices. As discussed above, imaging systems may be used with various protocols. Each protocol may include a number of different settings, or as referred to herein, parameters. For example, a given protocol may require various settings including a tube current, tube voltage, filter usage, filter type, and the like. However, the parameters in a given protocol may be specific to a given first imaging device. When second imaging device is used, parameters of a protocol from a previous imaging device may be translated by determining adjustments to be made to the parameters at the second imaging device. The technical effect is that protocol translation may be enabled allowing users of the techniques described herein a way to quickly transition between imaging devices.

It should be noted that although the various embodiments are described in connection with a particular diagnostic medical imaging system, such as an X-ray computed tomography (x-ray CT) detector system, the various embodiments may be implemented in connection with other imaging systems, such as a Positron Emission Tomography (PET) imaging system. Additionally, the imaging system may be used to image different objects, including objects other than people.

Figure 1:
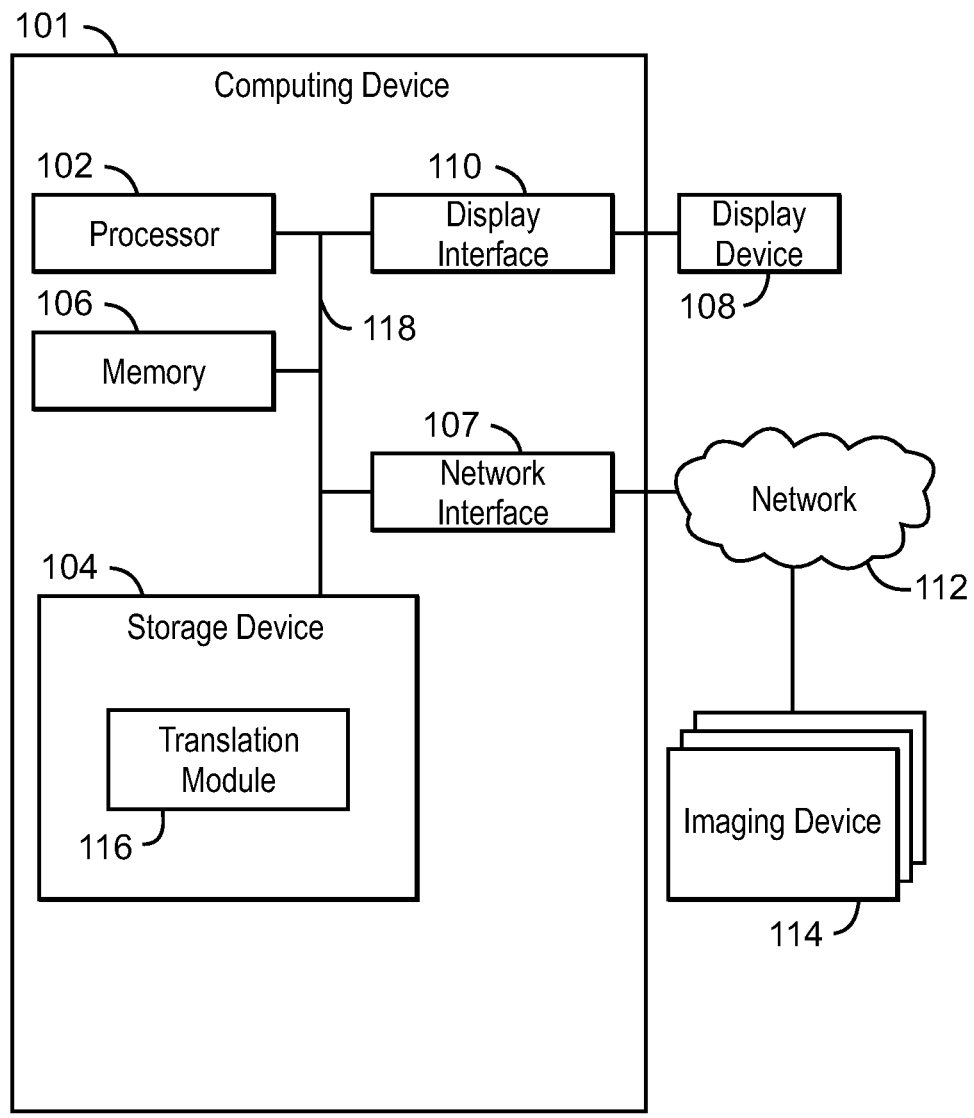
FIG. 1 illustrates a block diagram illustrating a computing system configured to translate imaging protocols.

FIG. 1 illustrates a block diagram illustrating a computing system configured to translate imaging protocols. The computing system 100 may include a computing device 101 having a processor 102, a storage device 104, a memory device 106, a network interface 107, a display device 108, and a display interface 110. The computing device 101 may communicate, via the network interface 107, with a network 112 to access a one or more imaging devices 114.

The storage device 104 may be a non-transitory computer-readable medium having a translation module 116. The translation module 116 may be implemented as logic, at least partially comprising hardware logic, as firmware embedded into a larger computing system, or any combination thereof. The translation module 116 is configured to receive data indicating a protocol for image capture of a first imaging device, such as one of the imaging devices 114. The protocol includes one or more parameters for imaging. The translation module 116 may also translate the protocol of the first imaging device for use at a second imaging device by determining adjustments to be made to one or more of the parameters.

The processor 102 may be a main processor that is adapted to execute the stored instructions. The processor 102 may be a single core processor, a multi-core processor, a computing cluster, or any number of other configurations. The processor 102 may be implemented as Complex Instruction Set Computer (CISC) or Reduced Instruction Set Computer (RISC) processors, x86 Instruction set compatible processors, multi-core, or any other microprocessor or central processing unit (CPU).

The memory device 106 can include random access memory (RAM) (e.g., static RAM, dynamic RAM, zero capacitor RAM, Silicon-Oxide-Nitride-Oxide-Silicon, embedded dynamic RAM, extended data out RAM, double data rate RAM, resistive RAM, parameter RAM, etc.), read only memory (ROM) (e.g., Mask ROM, parameter ROM, erasable programmable ROM, electrically erasable programmable ROM, etc.), flash memory, or any other suitable memory systems. The main processor 102 may be connected through a system bus 118 (e.g., PCI, ISA, PCI-Express, etc.) to the network interface 107. The network interface 107 may enable the computing device 101 to communicate, via the network 112, with the imaging devices 114.

In embodiments, the computing device 101 may render images at the display device 108, via the display interface 110. The display device 108 may an integrated component of the computing device 101, a remote component such as an external monitor, or any other configuration enabling the computing device 101 to render a graphical user interface. As discussed in more detail below, a graphical user interface rendered at the display device 108 may be used in image protocol translation techniques.

The block diagram of FIG. 1 is not intended to indicate that the computing device 101 is to include all of the components shown in FIG. 1. Further, the computing device 101 may include any number of additional components not shown in FIG. 1, depending on the details of the specific implementation.

Figure 2:
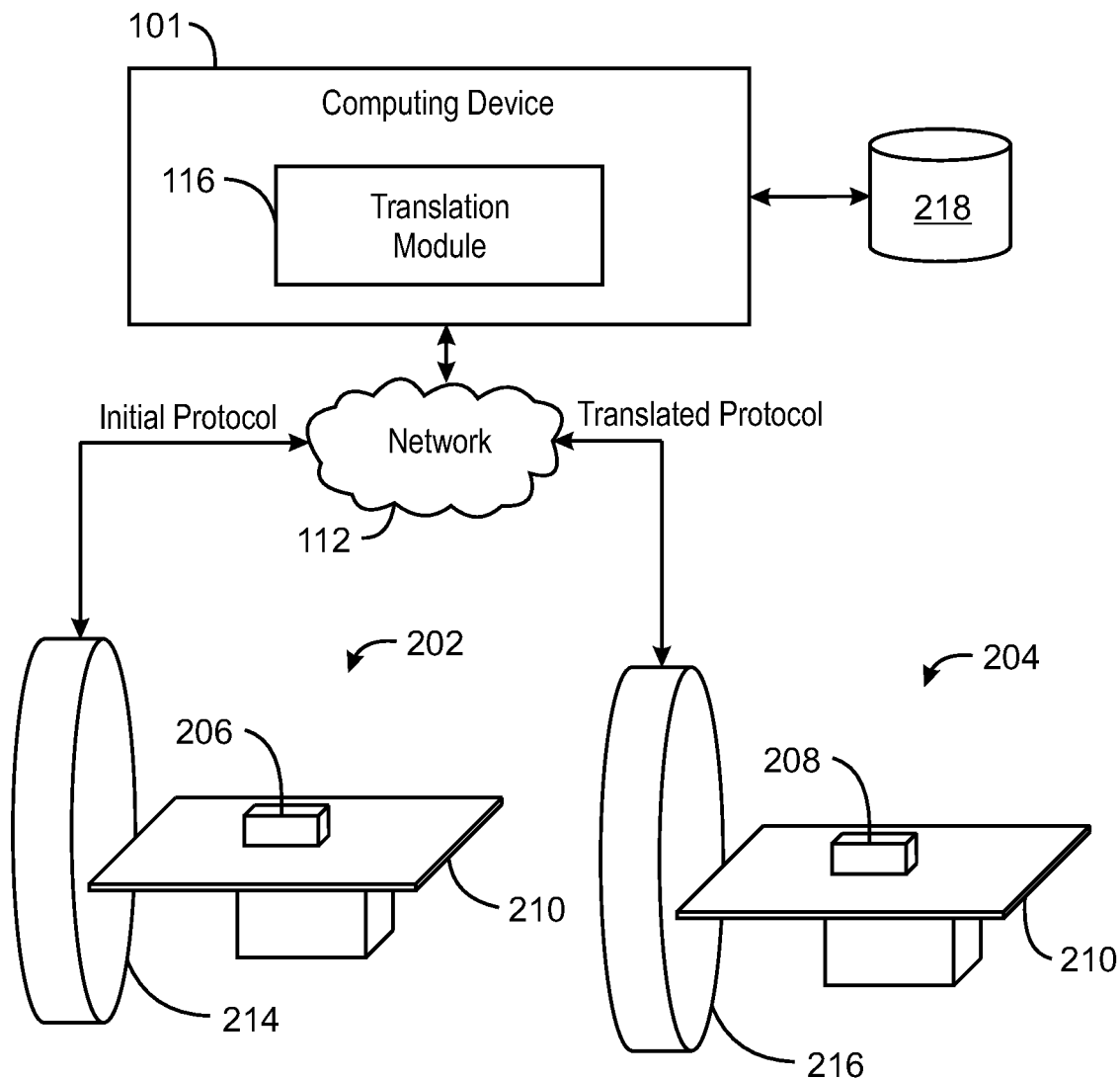
FIG. 2 illustrates a diagram of a system for translating protocols from a first imaging device to a second imaging device.

FIG. 2 illustrates a diagram of a system for translating protocols from a first imaging device to a second imaging device. As illustrated in FIG. 2, the system 200 includes a first imaging device 202 and a second imaging device 204. Protocols of the first imaging device 202 may be provided to the computing device 101 via the network 112. In some scenarios, the first imaging device 202 and the second imaging device 204 may be directly communicatively coupled to the computing device 101. In any case, the translation module 116 may translate protocols from the first imaging device 202 for use at the second imaging device 204.

As discussed above, each protocol of the first imaging device 202 may include one or more parameters such as tube current, tube voltage, filter use, filter type, scan speed, and the like, that are specific to each protocol associated with the first imaging device 202. However, the second imaging device 204 may require adjustments to the parameters of any given protocol associated with the first imaging device 202.

In embodiments, the translation module may determine adjustments to be made to one or more parameters of a protocol of associated with the first imaging device 202 by receiving data indicating a desired metric for an image capture at the second imaging device 204. A desired metric may include an image quality metric, a radiation dose metric, or a combination of an image quality metric and a radiation dose metric. This combined metric could be automatically selected during the protocol conversion process based on the type of protocol being converted, or could be manually selected by a user.

An image quality metric, as referred to herein, is a quantifiable metric of an image captured using an imaging device. The image quality metric may include sub-metrics related to various aspects of an image such as image noise, image contrast, spatial resolution, texture, artifacts, and the like. The image quality metric may reflect a single sub-metric of image quality, or may be a weighted combination of multiple sub-metrics. The translation module 116 may be configurable to receive image quality metrics from a user of the system 200. As discussed in more detail below, inputs may be received via a human input output device, such as a keyboard, a mouse, a touchscreen, and the like, via a graphical user interface rendered at a display device, such as the display device 108 discussed above in regard to FIG. 1.

In addition to image quality and dose metrics, a set of rules may be used to create a hierarchy for parameter selection at block 315. This may be required since there may be multiple ways that an equivalent protocol could be achieved. For instance, if spatial resolution is of primary concern in an inner ear scan, parameters that impact this metric (e.g., reconstruction kernel) may be prioritized in the translation process, which could have implications on the selection of the remaining parameters. Alternatively, if patient motion is of primary concern, parameters that impact imaging speed (e.g., rotation speed) may be prioritized in the translation process. Each parameter that is selected in the translation process is constrained by the prioritized parameters. In some cases, the prioritized parameters are selected before other parameters are translated. In this scenario, each parameter that is selected is constrained by previously selected parameters. In embodiments, one or more metrics may be prioritized based on a type of image capture. For example, the inner ear scan discussed above may prioritize spatial resolution by selecting a type of reconstruction and reconstruction filter. In this case, spatial resolution may be selected first, while additional parameters selected afterwards are constrained by the previously selected spatial resolution parameters.

As indicated in FIG. 2, an initial protocol may be provided to the translation module 116 from the first imaging device 202. The adjustments to be made to one or more of the parameters of the initial protocol may be based on predetermined image capture data stored in a database 218. The predetermined image capture data may include image capture data of test objects, such as the test object 206 and 208. The test objects 206 and 208 are imaged at each device 202, 204. In one example, the test objects 206 and 208 may be placed on pallets 210 and 212, respectively. The pallets 210 and 212 can move the respective test objects 206 and 208 horizontally for locating the test objects 206 and 208 in to gantries 214 and 216 of each respective imaging device 202 and 204. In other examples, the test objects 206 and 208 may be placed on a patient cradle, or some other support device.

The test objects 206 and 208 may be used to capture images at each of the first and second imaging devices 202 and 204, respectively. In embodiments, the test objects 206 and 208 are substantially similar to one another. As the test objects 206 and 208 are substantially similar to one another, the differences in image metrics between images captured of the test object 206 at the first imaging device 202 and images captured at the test object 208 at the second imaging device 204 may indicate parameters that can be adjusted at the second imaging device.

For example, an image of the test object 206 may be performed using the initial protocol including a tube current parameter of 300 milliamperes (mA). The image of the test object 206 may have an image noise metric of 30 Hounsfield Units (HU). However, an image of the test object 208 using the initial protocol at the second imaging device 204 may result in a noise metric of 42.4 HU. In this scenario, the mA parameter may be adjusted to 600 mA in the translated protocol. Other methods of building predetermined image capture data may be used.

In some scenarios, predetermined image capture data may include data of previously scanned patients from the first image capture device. For example, in a hospital setting, images from previous patients may be stored on the computing device 101, and metrics may be determined based on stored images. Protocols and their associated parameters may be stored at the database 218 on the computing device for each of the previously scanned patient image.

In some scenarios, predetermined image capture data may include specifications provided by a manufacturer of the imaging devices 202 and 204. For example, the first image capture device 202 may have a tube voltage capability of 100 kVp, while the second image capture device 204 may have a tube voltage capability of 80 kVp. Therefore, an initial protocol of the first imaging device 202 including 100 kVp may be translated to 80 kVp with modified tube current.

Figure 3:
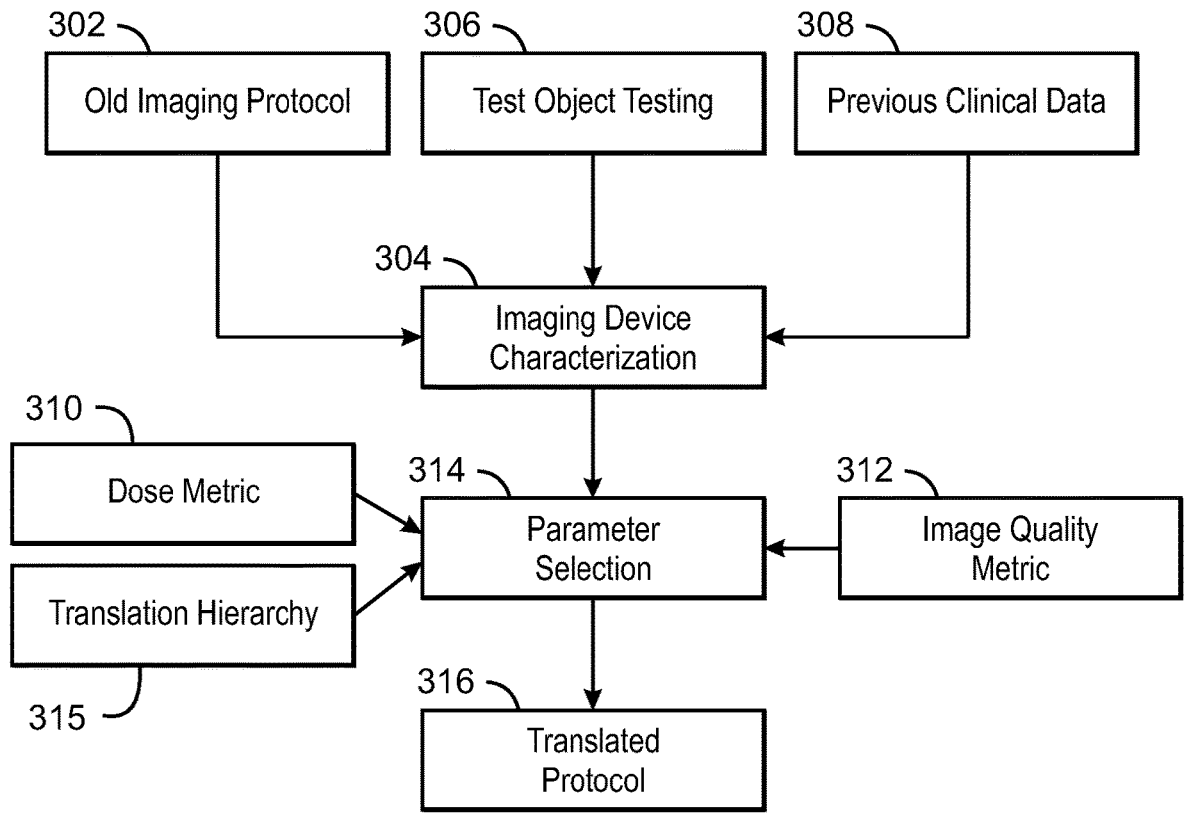
FIG. 3 illustrates a graphical user interface to render a translation of an imaging protocol.

FIG. 3 illustrates a process flow diagram for translating an imaging protocol. An old imaging protocol, indicated at 302, may be characterized at 304 based on predetermined image capture data including test object testing at 306, and/or previous clinical data 308. The old imaging protocol 302 may be associated with a first imaging device, such as the first imaging device 202 of FIG. 2. As discussed above in regard to FIG. 2, test objects, such as the test objects 206 and 208, may be used to establish predetermined image capture data at block 306. In some cases, previous clinical data may be used, as indicated at 308. In some cases, simulations of test objects may be used. The imaging device characterization 304 may include detailing the parameters used in a given image capture via the test object testing 306, the previous clinical data 308, or any combination thereof. The imaging device characterization 304 may also identify metrics of previously performed image captures. The parameters of previously performed image captures may be stored in a database, such as the database 218 of FIG. 2. In embodiments, the characterization performed at 304 may be the act of building the database 218 including the parameters of the old imaging protocol, metrics including radiation dose metrics and image quality metrics an image captured using the old imaging protocol.

At 310 and 312, metrics are selected for a new image to be captured using a second imaging device, such as the second imaging device 204 of FIG. 2. Based on the dose metric 310, the image quality metric 312, or any combination of the dose metric 310 and the image quality metric 312, parameters are selected at 314 to produce a translated protocol at 316. As discussed above, the translated protocol at 316 may include at least one parameter that has been adjusted based on one or more of the dose metric selected at 310, the image quality metric selected at 312, and in view of the imaging device characterization 304.

For example, the old protocol 302 may be a protocol to scan an abdomen for a patient. The test object testing at 306 may include testing of a plurality of test objects at each of the first imaging device 202 and the second imaging device 204. The plurality of test objects may include a 10 centimeter (cm) container of water, a 20 cm container of water, a 30 cm container of water, and a 40 cm container of water. The first imaging device 202 may be characterized by determining the parameters of the abdomen protocol, and the image quality and dose metrics associated with the resulting images of the test object testing 306. Similarly, images of the same or similar test objects may be captured by the second imaging device 204, and a characterization may be performed of the second imaging device 204 based on the images and their associated metrics. Correlations between images may be identified by matching metrics. Adjustments to the parameters of the abdomen protocol may be made at the parameter selection 314. For example, the parameter selection 316 may adjust one or more parameters of the abdomen protocol such as slice thickness, tube voltage, tube current, a focal spot size, a beam filter, an amount of noise reduction, image noise, among others.

As discussed in more detail below in regard to FIG. 4, the translation may be rendered in a graphical user interface. In some scenarios where a translation does not exactly match dose and image quality metrics, a user may provide an allowable range of deviation. Further, in some cases, more than one metric may be specified by a user. In these scenarios, the user may rank the metrics, and multiple ranked protocols may be provided.

Figure 4:
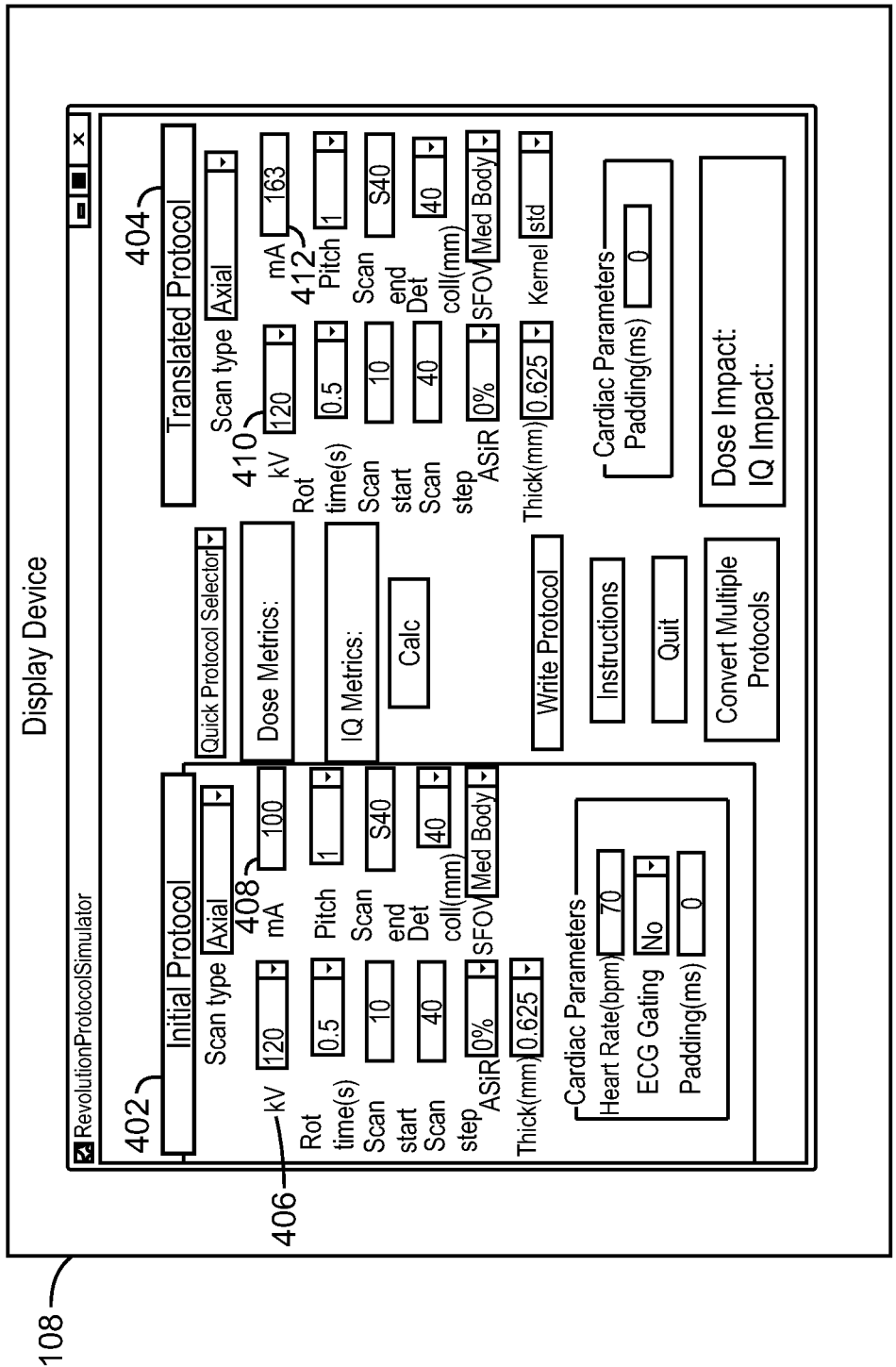
FIG. 4 illustrates a graphical user interface to render a translation of an imaging protocol.

FIG. 4 illustrates a graphical user interface to render a translation of an imaging protocol. The graphical user interface 400 may be rendered at a display device, such as the display device 108 of FIG. 1. As illustrated in FIG. 4, the graphical user interface 400 may display a translation from an initial protocol 402 to a translated protocol 404. Various parameters may be displayed at the graphical user interface 400 in both protocols 402, 404. For example, the kVp parameter 406 and the milliamp (mA) parameter 408 of the initial protocol are shown. At 408 the translated protocol includes the kVp parameter at 410 and the adjusted mA parameter 412.

As illustrated in FIG. 4, a given protocol may include several parameters. For example, other parameters may include a rotation time, a pitch, a scan start position, a scan stop position, a scan step setting, beam collimation, whether a reconstruction filter is used and/or filter type, a scan field of view, a thickness of a beam filter, and the like. Further parameters may also include heart rate monitoring of a patient to be scanned, an electrocardiograph gating setting, a padding, and the like. Further, the graphical user interface 400 may enable a user to quickly determine adjustments to parameters when switching between imaging devices, such as the imaging devices 402 and 404 of FIG. 2. The translation may be based on the image capture and comparison data discussed above with regard to FIG. 4.

Although not illustrated in FIG. 4, in some scenarios, the graphical user interface 400 may enable a user to rank image quality metrics such that translated protocols may be displayed in based on the rank. This may be useful when two imaging devices do not have the same parameters available.

For example, a first scanner may have 3 filters available and a second scanner may only have 2 filters available. In this scenario, a ranking of image quality metrics and/or dose metrics that may be important to the user may be input by the user. The resulting translation may be based on the ranking such that the translation most closely matching the desired clinical behavior corresponding to the translation rules may be presented at the top of the ranking. As discussed above, the translation, and the ranking may be based on available predetermined image capture data, such as test object data performed at both the first and second scanner 202 and 204 of FIG. 2.

Figure 5:
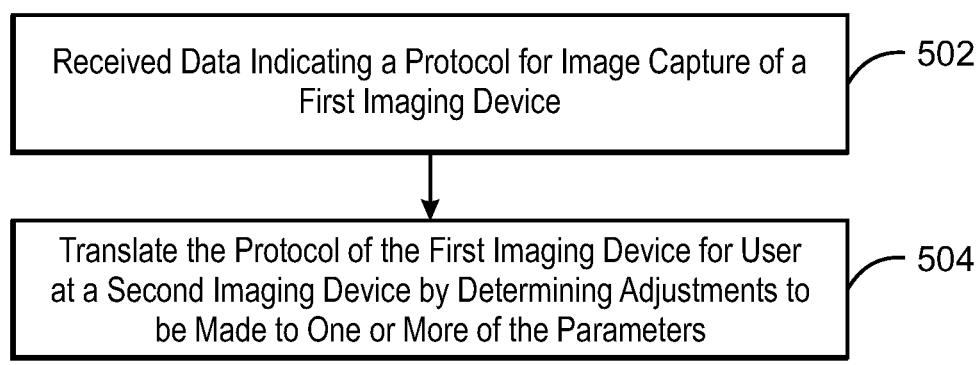
FIG. 5 is a block diagram illustrating a method of translating imaging protocols.

FIG. 5 is a block diagram illustrating a method of translating imaging protocols. The method 500 may include receiving data indicating a protocol for image capture at block 502. The protocol may be associated with a first imaging device. The protocol may include one or more parameters. At block 504, the protocol of the first imaging device may be translated for use at a second imaging device by determining adjustments to be made to one or more of the parameters.

Determining the adjustments may include receiving data indicating a desired metric for an image capture to be performed at the second imaging device. The desired metric may be received via a graphical user interface, such as the graphical user interface 400 of FIG. 4. The method 500 may include determining one or more parameters to be adjusted based on the desired metric.

Figure 6:
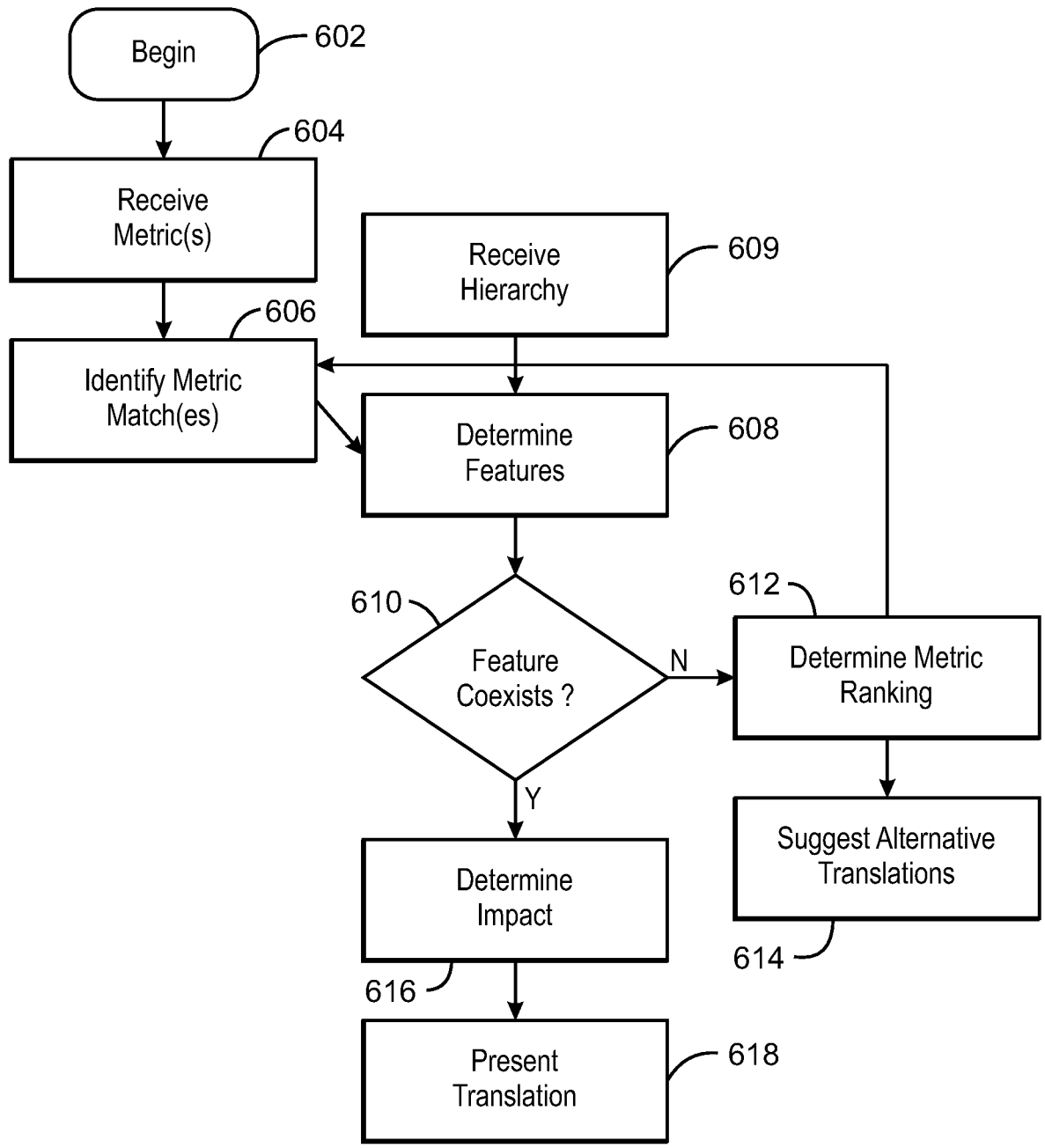
FIG. 6 is a flow diagram of a process of translating imaging protocols.

FIG. 6 is a flow diagram of a process of translating imaging protocols. The process 600 begins at 602. At 604 metrics are received. The metrics may be identified based on a user input, for example. The metrics may be desired metrics including a desired image metric and a desired dose metric. At 606, metric matches are identified. The metric matches may be identified from querying a database of pre-captured images, such as the database 218 discussed above in regard to FIG. 2. Once metrics have been matched, features of each imaging device may be determined 608. In some embodiments, the features may be determined by a reference to document providing specifications from a manufacturer. In other embodiments, the features may be extrapolated from the image capture data discussed above in reference to FIG. 2 and FIG. 3. For example, in a given protocol, an image noise metric of an image captured at the second imaging device may be half of an image noise metric of an image captured at a first imaging device for a given protocol, all other parameters being equal. In this scenario, the second imaging device may be assumed to have a relatively lower tube current requirement in comparison to the first imaging device.

In some embodiments, a hierarchy of rules may be received at 609. In this scenario, the hierarchy may indicate parameters to prioritize in the translation process 600 based on a given imaging capture type. In some scenarios, the hierarchy may indicate a value, such as an image metric, to prioritize first in view of the image metric received at 604. For example, an inner ear scan may focus on spatial resolution. In this scenario, a filter specific to a high spatial resolution result would be selected first, while subsequent parameters may be constrained by the filter selection in view of the image metric received at 604. In other words, the hierarchy may select one or more parameters based on a given focus, including an image metric, in addition to the metric received at 604. Once the parameters are selected based on the hierarchy, the process 600 may continue to translate parameters in view of the image metric received at 604. Additional details relating to the hierarchy received at 609 are discussed below in regard to FIG. 7.

At 610, it is determined whether features coexist on both imaging devices. For example, a first imaging device may have filters that are not available on a second imaging device. Therefore, if features do not coexist, alternative translations may be identified. The alternative translations may be based on rankings determined at 612. Once the rankings are determined at 612, the process 600 may cycle back to identifying metric matches 606 that most closely match the ranking determined at 612. In some cases, user-input may provide a range of acceptable metric deviations for each ranked metric. Once alternative translations have been determined at 612, alternative translations based on the rankings are suggested at 614.

If the features do coexist at 610, the process continues at 616 wherein the impact between the capabilities of a given feature at the second imaging device may have on captured images. As discussed above, if the tube current requirement of the second imaging device is half of the tube current capability of the first imaging device, the impact determination for a given protocol may indicate that the tube current must be reduced by half at the second imaging device to produce the desired metric received at 604. At 618, the translation is presented indicating an adjustment in a given parameter to reach the desired metric received at 604. In another example, a reconstruction type and kernel may first be chosen to provide a similar spatial resolution in the image. Then a slice thickness may be chosen to provide a similar response. Beam filtration and tube voltage may then be selected to provide similar image contrast. Tube current may then be chosen based on the combined impact of all of the parameters on the image quality and dose metrics of interest.

Figure 7:
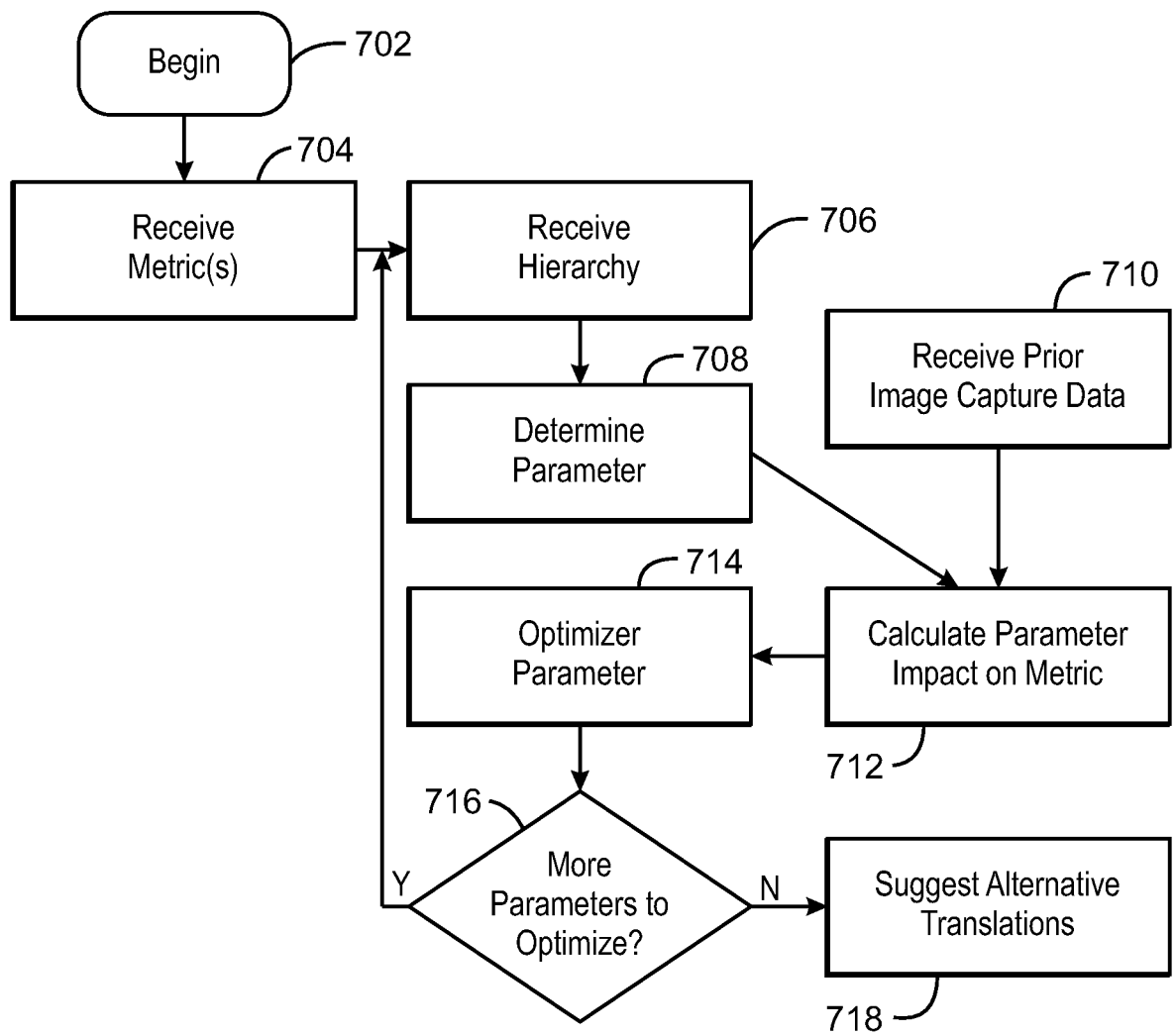
FIG. 7 is a flow diagram illustrating a process of translating imaging protocols in view of a hierarchy.

FIG. 7 is a flow diagram illustrating a process of translating imaging protocols in view of a hierarchy. The process 700 begins at 702, and at 704, metrics, such as dose metrics, image metrics, are received. At 706, a hierarchy is received. The hierarchy is a prioritization based on input from a user. For example, in some imaging scenarios, such as in a pediatric environment, movement of the imaging subject may be a concern. In this scenario, a user may select motion artifact minimization as a priority. Other priorities may be selected as well. When two or more priorities are selected, the user input may indicate a weighting for the priorities, such that a higher weighted priority may be addressed first in the process 700.

At block 708, a parameter associated with a given priority is determined For example, if the motion artifact minimization is indicated in the hierarchy 706, a parameter, such as image scan speed may be determined to reduce movement of a resulting image.

At block 710, previous image capture data is received. As discussed above in regard to FIG. 1 and FIG. 2, previous image capture data may be used to calculate an impact that the parameter determined at 708 has on the metric identified at 704. The impact calculation may be performed at block 712.

At block 714, the parameter determined at 708 may be optimized. For example, the optimization may be in view of the metrics received at 704. In some cases where the hierarchy includes more than one prioritization, additional metrics may be indicated. At block 716, the process 700 determines whether more parameters are indicated by a prioritization hierarchy received at 706. If yes, the next parameter is determined based on the prioritization hierarchy at block 708. If the hierarchy does not indicate additional parameters, the translation of parameters is presented at 718.

Examples provided above include prioritization of parameters to reduce the impact of image movement. In some scenarios, a faster scan speed of a new scanner may indicate a different parameter that may need to be adjusted based on the hierarchy received at block 706. More specifically, if scanner A has a protocol for a liver scan that indicates a 120 kV tube current at 300 mA for 1 second. The new scanner may rotate faster, indicating that a higher mA is needed to get the same signal. Therefore, a translation may include 120 kV at 400 mA for 0.75 s.

As another example, movement impact may be indicated by a given level of image sharpness. In this example, the parameter determination 708 may include identifying an acceptable threshold of image sharpness.

Other prioritizations in the hierarchy are contemplated. For example, the metrics received at 704 may indicate a combination of an image contrast value and image noise value. The hierarchy may include a first priority indicating a desired limiting of radiation dose level, and a second priority indicating a reduction of motion artifacts is desired. In this scenario, scanner A for a pediatric abdomen may include 80 kV at 200 mA, among other parameters. Scanner B may have lower kV capabilities. Therefore, the translation may adjust kV and mA, such as 70 kV at 300 mA.

In another example, the metrics may include a combination of image noise, spatial resolution, and image texture. The hierarchy may include a first priority of edge sharpness, a second priority of artifacts, and a third priority of radiation dose. Scanner A protocol for an inner ear may be 120 kV, 200 mA, and a bone kernel filter. Scanner B has a different kernel filter that may improve bone images when compared to the bone kernel filter of Scanner A, but impacts the amount of signal that is required. Therefore, the impact may be accounted for such that the scanner B protocol includes 120 kV, 300 mA, and a "bone plus" kernel.

In another example, the metrics received at 704 may include a combination of image contrast and noise. The hierarchy received at 706 may have a first priority of dose, then a second priority of minimal impact from patient motion. In this scenario, scanner A protocol for pediatric abomen, may include 80 kV, 200 mA, a helical pitch of 1, and the like. Scanner B may have a wider scan coverage such that a helical pitch can be translated to a single axial acquisition. The translated protocol may adjust kV, mA, and scan type, such as 70 kV, 300 mA, and axial at wide coverage.

Figure 8:
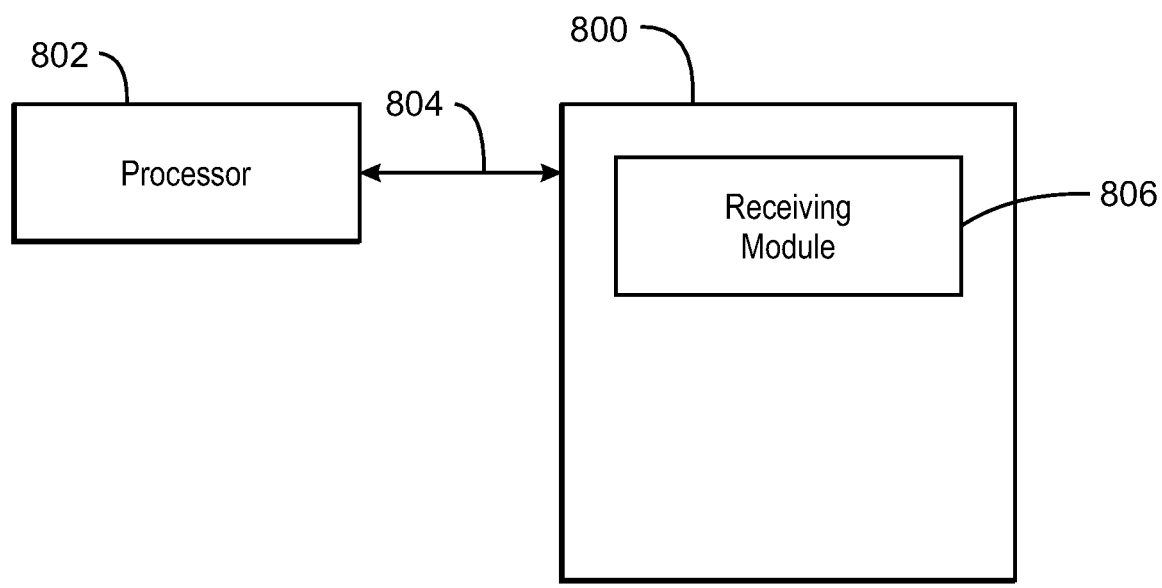
FIG. 8 is a block diagram of a computer readable medium that includes modules for translating imaging protocols.

FIG. 8 is a block diagram of a computer readable medium that includes modules for translating imaging protocols. The computer readable medium 800 may be a non-transitory computer readable medium, a storage device configured to store executable instructions, or any combination thereof. In any case, the computer-readable medium is not configured as a carry wave or a signal.

The computer-readable medium 800 includes code adapted to direct a processor 802 to perform actions. The processor 802 accesses the modules over a system bus 804.

A translation module 806 may be configured to receive data indicating a protocol for image capture of a first imaging device, wherein the protocol comprises parameters. The translation module 806 may also be configured to translate the protocol of the first imaging device for use at a second imaging device by determining adjustments to be made to one or more of the parameters.

While the detailed drawings and specific examples given describe particular embodiments, they serve the purpose of illustration only. The systems and methods shown and described are not limited to the precise details and conditions provided herein. Rather, any number of substitutions, modifications, changes, and/or omissions may be made in the design, operating conditions, and arrangements of the embodiments described herein without departing from the spirit of the present techniques as expressed in the appended claims.

This written description uses examples to disclose the techniques described herein, including the best mode, and also to enable any person skilled in the art to practice the techniques described herein, including making and using any devices or systems and performing any incorporated methods. The patentable scope of the techniques described herein is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method for imaging protocol translation, comprising:
   receiving, at a processor, data indicating a protocol for image capture of a first imaging device, wherein the protocol comprises parameters;
   translating, via the processor, the protocol of the first imaging device into a plurality of translated protocols for use at a second imaging device by automatically determining adjustments to be made to one or more of the parameters to achieve a specific image quality during capture of an image with the second imaging device utilizing a translated protocol from the plurality of translated protocols, wherein determining the adjustments comprises receiving data indicating a desired metric for an image capture at the second imaging device and determining one or more parameters of the protocol to adjust based on the desired metric, the desired metric comprising at least one of an image quality metric or a radiation dose metric, and wherein the first imaging device is different from and physically separate from the second imaging device, and the first and second imaging devices are of the same imaging modality;
   rendering, at a graphical user interface, the protocol and its one or more parameters and the plurality of translated protocols and their one or more parameters including the adjusted one or more parameters; and
   rendering, at the graphical user interface, the plurality of translated protocols based on a desired ranking of metrics for the image capture at the second imaging device, wherein the metrics comprise the desired metric, and wherein the plurality of translated protocols are rendered on the graphical user interface in ranked order.

2. The method of claim 1, further comprising:
   generating data indicating a parameter selection rules hierarchy for an image capture at the second imaging device; and
   determining one or more parameters of the protocol to adjust based on an optimization using the hierarchy.

3. The method of claim 1, wherein determining the adjustments to be made to one or more of the parameters is based on predetermined image capture data.

4. The method of claim 3, wherein the predetermined image capture data comprises:

image capture data of test objects performed at one or more of the imaging devices;
image capture data of previously scanned patients from the first image capture device;
specifications of a manufacturer of one or more of the image capture devices; or
any combination thereof.

5. A system for imaging protocol translation, comprising:
a processing device;
a protocol translation module comprising logic that when executed by the processing device causes the processing device to:
receive data indicating a protocol for image capture of a first imaging device, wherein the protocol comprises parameters;
translate the protocol of the first imaging device into a plurality of translated protocols for use at a second imaging device by automatically determining adjustments to be made to one or more of the parameters to achieve a specific image quality during capture of an image with the second imaging device utilizing a translated protocol from the plurality of translated protocols, wherein determining the adjustments comprises receiving data indicating a desired metric for an image capture at the second imaging device and determining one or more parameters of the protocol to adjust based on the desired metric, the desired metric comprising at least one of an image quality metric or a radiation dose metric, and wherein the first imaging device is different from and physically separate from the second imaging device, and the first and second imaging devices are of the same imaging modality;
render, at a graphical user interface, the protocol and its one or more parameters and the plurality of translated protocols and their one or more parameters including the adjusted one or more parameters; and
render, at the graphical user interface, the plurality of translated protocols based on a desired ranking of metrics for the image capture at the second imaging device, wherein the metrics comprise the desired metric, and wherein the plurality of translated protocols are rendered on the graphical user interface in ranked order.

6. The system of claim 5, wherein translation further comprises:
generating data indicating a parameter selection rules hierarchy for an image capture at the second imaging device; and
determining one or more parameters of the protocol to adjust based on an optimization using the hierarchy.

7. The system of claim 5, wherein determining the adjustments to be made to one or more of the parameters is based on predetermined image capture data.

8. The system of claim 7, wherein the predetermined image capture data comprises:
image capture data of test objects performed at one or more of the image capture devices;
image capture data of previously scanned patients from the first image capture device;
specifications of a manufacturer of one or more of the image capture devices; or
any combination thereof.

9. A non-transitory computer-readable medium for imaging protocol determination, the computer-readable medium comprising processor-executable code that when executed by a processor causes the processor to:
receive data indicating a protocol for image capture of a first imaging device, wherein the protocol comprises parameters;
translate the protocol of the first imaging device into a plurality of translated protocols for use at a second imaging device by automatically determining adjustments to be made to one or more of the parameters to achieve a specific image quality during capture of an image with the second imaging device utilizing a translated protocol from the plurality of translated protocols, wherein determining the adjustments comprises receiving data indicating a desired metric for an image capture at the second imaging device and determining one or more parameters of the protocol to adjust based on the desired metric, the desired metric comprising at least one of an image quality metric or a radiation dose metric, and wherein the first imaging device is different from and physically separate from the second imaging device, and the first and second imaging devices are of the same imaging modality;
render, at a graphical user interface, the protocol and its one or more parameters and the plurality of translated protocols and their one or more parameters including the adjusted one or more parameters; and
render, at the graphical user interface, the plurality of translated protocols based on a desired ranking of metrics for an image capture at the second imaging device, wherein the metrics comprise the desired metric, and wherein the plurality of translated protocols are rendered on the graphical user interface in ranked order.

10. The non-transitory computer-readable medium of claim 9, wherein the translation further comprises:
generating data indicating a parameter selection rules hierarchy for an image capture at the second imaging device; and
determining one or more parameters of the protocol to adjust based on an optimization using the hierarchy.

11. The non-transitory computer-readable medium of claim 9, wherein determining the adjustments to be made to one or more of the parameters may be based on predetermined image capture data.

12. The non-transitory computer-readable medium of claim 11, wherein the predetermined image capture data comprises:
image capture data of test objects performed at one or more of the image capture devices;
image capture data of previously scanned patients from the first image capture device;
specifications of a manufacturer of one or more of the image capture devices; or
any combination thereof.

13. The method of claim 1, further comprising receiving, at the processor, an input selecting the translated protocol on the graphical user interface for utilization in image capture.

14. The system of claim 5, wherein when the logic is executed by the processing device further causes the processing device to receive an input selecting the translated protocol on the graphical user interface for utilization in image capture.

15. The non-transitory computer-readable medium of claim 9, wherein the processor-executable code when executed by the processor further causes the processor to receive an input selecting the translated protocol on the graphical user interface for utilization in image capture.

* * * * *